(12) United States Patent
Wayman et al.

(10) Patent No.: US 8,540,670 B2
(45) Date of Patent: Sep. 24, 2013

(54) PASSIVE REUSE PREVENTION SYRINGE THAT USES A RETAINING RING LOCK

(75) Inventors: Brian H. Wayman, Morris Plains, NJ (US); Robert Odell, Franklin Lakes, NJ (US); Richard James Caizza, Vernon, NH (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 186 days.

(21) Appl. No.: 12/492,554

(22) Filed: Jun. 26, 2009

(65) Prior Publication Data

US 2009/0326451 A1 Dec. 31, 2009

Related U.S. Application Data

(60) Provisional application No. 61/075,941, filed on Jun. 26, 2008.

(51) Int. Cl.
*A61M 5/00* (2006.01)
*A61M 5/315* (2006.01)

(52) U.S. Cl.
USPC .......................... 604/110; 604/187; 604/218

(58) Field of Classification Search
USPC ................ 604/110, 187, 218, 311; 600/15
See application file for complete search history.

(56) References Cited

U.S. PATENT DOCUMENTS

| | | | |
|---|---|---|---|
| 4,248,228 A * | 2/1981 | Silver | 604/192 |
| 4,713,056 A * | 12/1987 | Butterfield | 604/110 |
| 4,747,830 A | 5/1988 | Gloyer et al. | |
| 4,986,812 A | 1/1991 | Perler | |
| 5,047,017 A | 9/1991 | Koska | |
| 5,125,899 A | 6/1992 | Frignoli | |
| 5,211,630 A | 5/1993 | Schmahmann | |
| 5,407,436 A * | 4/1995 | Toft et al. | 604/195 |
| 5,527,284 A | 6/1996 | Ohnemus et al. | |

(Continued)

FOREIGN PATENT DOCUMENTS

| EP | 1106194 | 6/2001 |
|---|---|---|
| EP | 1106194 A1 * | 6/2001 |

(Continued)

OTHER PUBLICATIONS

Photos of Kojak Selinge (Star Syringe K1) Auto-Disable Syringe with Disposable Needle.

(Continued)

*Primary Examiner* — Nicholas Lucchesi
*Assistant Examiner* — Leah Stohr
(74) *Attorney, Agent, or Firm* — The Webb Law Firm

(57) ABSTRACT

A syringe assembly includes a syringe barrel having an inside surface defining a chamber and an outlet. A plunger assembly is disposed within the syringe barrel and includes an elongate plunger rod having a distal end surface, a plunger head having a distal sealing surface and a proximal end surface having a continuous perimeter, and a breakable neck portion integrally connecting the plunger rod and the plunger head. A retaining ring lock is disposed on the inside surface of the barrel and defines an engagement surface about a perimeter of the chamber. The retaining ring lock is adapted to engage and retain the plunger head in a locked position within the chamber. The engagement surface of the retaining ring lock engages the continuous perimeter of the proximal end surface of the plunger head in a perimetrical engagement when the plunger head is in the locked position.

18 Claims, 8 Drawing Sheets

(56) References Cited

U.S. PATENT DOCUMENTS

| | | | |
|---|---|---|---|
| 5,531,693 A * | 7/1996 | Vounatsos | 604/110 |
| 5,562,623 A | 10/1996 | Shonfeld et al. | |
| 5,814,017 A * | 9/1998 | Kashmer | 604/110 |
| 6,117,112 A | 9/2000 | Mahurkar | |
| 6,267,749 B1 | 7/2001 | Miklos et al. | |
| 6,368,306 B1 | 4/2002 | Koska | |
| 6,790,197 B2 | 9/2004 | Kosinski et al. | |
| 7,282,042 B2 | 10/2007 | Wang | |
| 7,766,882 B2 * | 8/2010 | Sudo et al. | 604/218 |
| 2004/0147875 A1 | 7/2004 | Wallace et al. | |
| 2005/0038394 A1 * | 2/2005 | Schwarzbich | 604/218 |
| 2005/0159705 A1 | 7/2005 | Crawford et al. | |
| 2006/0064060 A1 | 3/2006 | Lin | |
| 2007/0106226 A1 | 5/2007 | Croll et al. | |
| 2007/0191785 A1 | 8/2007 | Barere et al. | |
| 2007/0299395 A1 | 12/2007 | Pelkey et al. | |
| 2008/0300550 A1 | 12/2008 | Schiller et al. | |
| 2009/0048560 A1 | 2/2009 | Caizza et al. | |
| 2009/0076450 A1 | 3/2009 | Caizza et al. | |
| 2009/0131869 A1 | 5/2009 | Caizza et al. | |

FOREIGN PATENT DOCUMENTS

| | | |
|---|---|---|
| JP | 02-147069 | 6/1990 |
| WO | 88/10127 | 12/1988 |
| WO | 98/03210 | 1/1998 |
| WO | 2005079893 | 9/2005 |
| WO | 2006097105 | 9/2006 |
| WO | 2008154616 | 12/2008 |
| WO | 2008154630 | 12/2008 |

OTHER PUBLICATIONS

Photos of Neomedic Neoject Auto-Disable Syringe.

Photos of KangKang Autodestruct Syringe.

Photos of Dr. Safe Auto-Destruct Syringe Set.

Kojak Selinge "HMD Injection Procedure" Instruction Sheet, pp. 1-2.

Pictures of 0.5ml safety syringe cady, http://www.emunio.dk/solution/cady/pictures.asp.

* cited by examiner

PASSIVE REUSE PREVENTION SYRINGE THAT USES A RETAINING RING LOCK

CROSS REFERENCE TO RELATED APPLICATIONS

This application claims benefit of U.S. Provisional Patent Application No. 61/075,941 entitled "Perceived Passive Reuse Prevention Syringe that Uses a Retaining Ring Lock" filed Jun. 26, 2008, the entire contents of which is herein incorporated by reference in its entirety.

BACKGROUND OF THE INVENTION

1. Field of the Invention

The present invention relates to a perceived passive reuse prevention syringe that uses a retaining ring lock. More specifically, the present invention relates to a syringe that includes a retaining ring on the inside surface of a syringe barrel for engaging a plunger head, which includes the sealing surface of a plunger assembly. After the plunger head has entered the locked position, attempting to withdraw the plunger assembly from the syringe barrel will result in the plunger assembly breaking into two pieces with the plunger head remaining in the syringe barrel.

2. Description of Related Art

In the United States and throughout the world, the multiple use of hypodermic syringe products that are intended for single use only is instrumental in drug abuse and more particularly, in the transfer of diseases. Intravenous drug users who routinely share and reuse syringes are a high risk group with respect to the AIDS virus. Also, the effects of multiple use are a major concern in under-developed countries where repeated use of syringe products may be responsible for the spread of many diseases. Reuse of the single use hypodermic syringe assemblies is also instrumental in the spread of drug abuse even in the absence of infection or disease.

Many attempts have been made to remedy this problem. Some of these attempts have required a specific act to destroy the syringe after use either by using a destructive device or providing a syringe assembly with frangible zones so that the syringe could be rendered inoperable by the application of force. Other attempts involve the inclusion of structure which would allow the destruction or defeating of the syringe function to a conscious act by the syringe user. Although many of these devices work quite well, they do require the specific intent of the user followed by the actual act to destroy or render the syringe inoperable. These devices are not effective with a user having the specific intent to reuse the hypodermic syringe.

Attempts have also been made to provide an automatic function to disable or render a syringe assembly inoperable after a single or select number of uses. However, such an automatic function is harder to provide because the means for rendering the syringe inoperable must not prevent its filling or use under normal conditions. Moreover, typical automatic locking and disabling devices only allow for a fixed dosage amount to be supplied by the syringe before the syringe is disabled.

SUMMARY OF THE INVENTION

Accordingly, there is a general need for a single use syringe that includes a locking and disabling mechanism that does not operate automatically but that is perceived by the user as an automatic or passive device such that even a user who has the specific intent to reuse the syringe will actuate the mechanism through normal use of the syringe without consciously realizing that the syringe has been disabled. Such a mechanism will limit the ability of users to reuse the syringe while avoiding the unnecessary costs and dosage limitations of automatic devices.

The present invention overcomes many of the deficiencies present in the prior art by providing a syringe that offers the utility of a traditional syringe along with reuse prevention features and requiring a low force required to activate the reuse prevention mechanism. According to an embodiment of the present invention, the syringe includes a passively perceived reuse prevention mechanism that is activated by the user through normal use of the syringe though the user may not be aware or realize that the mechanism has been activated. The syringe allows for variable dosing, which is important for some procedures, but can also be adapted to deliver fixed doses if required and can be used for injections and/or reconstitution of dry drugs. The syringe is scaleable from the smallest syringe sizes to the largest syringe sizes and allows for reductions of cost compared to current reuse prevention syringes. The syringe is provided with a single piece plunger assembly having a sealing surface on a plunger head, which is engaged by the locking mechanism, such that there is no need for an expensive rubber stopper or plug on the plunger for sealing the syringe barrel, which reduces the material and manufacturing costs. Further, the single piece plunger has a breakable portion integrally molded so that the syringe will become disabled if an attempt is made to reuse the syringe after the plunger head has entered a locked position.

According to an embodiment of the present invention, a syringe assembly is provided. The syringe assembly includes a syringe barrel having an inside surface defining a chamber, an open proximal end, a distal end, and an outlet disposed adjacent the distal end in fluid communication with the chamber; a plunger assembly disposed at least partially within the syringe barrel that includes an elongate plunger rod having a distal end surface; a plunger head having a distal sealing surface and a proximal end surface, the proximal end surface of the plunger head having a continuous perimeter; a breakable neck portion extending between the distal end surface of the plunger rod and the proximal end surface of the plunger head, the plunger rod and the plunger head being integrally connected by the breakable neck portion; and a retaining ring lock disposed on the inside surface of the barrel and extending into the chamber of the barrel and defining an engagement surface about a perimeter of the chamber of the barrel, the retaining ring lock adapted to engage and retain the plunger head in a locked position at least partially within the chamber of the barrel, while allowing the plunger rod to be removed from the chamber of the barrel. The engagement surface of the retaining ring lock engages the continuous perimeter of the proximal end surface of the plunger head in a perimetrical engagement when the plunger head is in the locked position.

The engagement surface of the retaining ring lock is continuous about the perimeter of the chamber of the barrel and the retaining ring lock engages the continuous perimeter of the proximal end surface of the plunger head in a continuous perimetrical engagement when the plunger head is in the locked position.

The plunger head has a width slightly greater than a width of the chamber of the barrel at the distal sealing surface. The barrel further includes an outwardly extending flange at the open proximal end thereof. The plunger rod includes an outwardly extending flange at a proximal end thereof.

The retaining ring lock is disposed within the chamber of the barrel adjacent the distal end of the barrel. The retaining ring lock retains the plunger head in the locked position within the chamber of the barrel adjacent the distal end of the barrel. The syringe assembly further includes a needle cannula in fluid communication with the chamber of the barrel.

The breakable neck portion includes a tapered portion. The breakable neck portion has a center disposed between the proximal end surface of the plunger head and the distal end surface of the plunger rod, and tapers from both the proximal end surface of the plunger head and the distal end surface of the plunger rod so as to have a reduced diameter at the center. The breakable neck portion is adapted to break upon application of a force to the plunger rod that is greater than a force necessary to at least partially aspirate the syringe, and less than a force necessary to withdraw the plunger head past the retaining ring lock.

The retaining ring lock is integral with the inside surface of the barrel. The retaining ring lock has a substantially V-shaped cross section, a proximal beveled surface of the retaining ring lock that engages the distal sealing surface of the plunger head such that the plunger head is slidable past the retaining ring lock in a distal direction, and the engagement surface of the retaining ring lock is a distal beveled surface of the retaining ring lock that engages the proximal end surface of the plunger head such that the plunger head is restrained from sliding past the retaining ring lock in a proximal direction.

Alternatively, the retaining ring lock has a substantially V-shaped cross-section with a rounded apex, a proximal surface of the retaining ring lock that engages the distal sealing surface of the plunger head such that the plunger head is slidable past the retaining ring lock in a distal direction, and the engagement surface of the retaining ring lock is a distal surface of the retaining ring lock that engages the proximal end surface of the plunger head such that the plunger head is restrained from sliding past the retaining ring lock in a proximal direction.

In a further alternative, the retaining ring lock has a substantially V-shaped cross-section with a flat apex, a curved proximal surface of the retaining ring lock that engages the distal sealing surface of the plunger head such that the plunger head is slidable past the retaining ring lock in a distal direction, and the engagement surface of the retaining ring lock is a curved distal surface of the retaining ring lock that engages the proximal end surface of the plunger head such that the plunger head is restrained from sliding past the retaining ring lock in a proximal direction.

According to a further embodiment of the present invention, a plunger assembly for a syringe is provided. The plunger assembly includes an elongate plunger rod having a distal end surface and a plunger head having a distal sealing surface and a proximal end surface, the proximal end surface of the plunger head having a continuous perimeter adapted to provide a perimetrical engagement with the syringe, and a breakable neck portion extending between the distal end surface of the plunger rod and the proximal end surface of the plunger head. The plunger rod and the plunger head are integrally connected by the breakable neck portion. The plunger rod includes an outwardly extending flange at a proximal end thereof.

The plunger head is adapted to engage a retaining ring lock disposed within a barrel of the syringe such that the plunger head is capable of being retained in a locked position at least partially within the barrel of the syringe, while the plunger rod is capable of being removed from the barrel of the syringe. The breakable neck portion is adapted to break upon application of a force to the plunger rod that is greater than a force necessary to at least partially aspirate the syringe, and less than a force necessary to withdraw the plunger head past the retaining ring lock. The plunger head has a width at the distal sealing surface greater than a width of the plunger head at the proximal end surface. The breakable neck portion includes a center disposed between the proximal end surface of the plunger head and the distal end surface of the plunger rod and tapered portions extending from both the proximal end surface of the plunger head and the distal end surface of the plunger rod so as to have a reduced diameter at the center.

According to a further embodiment of the present invention, a method of actuating a syringe assembly is provided. The method includes the steps of providing a syringe assembly that includes a syringe barrel having an inside surface defining a chamber, an open proximal end, a distal end, and an outlet disposed adjacent the distal end in fluid communication with the chamber; a plunger assembly disposed at least partially within the syringe barrel, including an elongate plunger rod having a distal end surface, a plunger head having a distal sealing surface, and a proximal end surface, the proximal end surface of the plunger head having a continuous perimeter; a breakable neck portion extending between the distal end surface of the plunger rod and the proximal end surface of the plunger head, the plunger rod and the plunger head being integrally connected by the breakable neck portion; and a retaining ring lock disposed on the inside surface of the barrel and extending into the chamber of the barrel and defining an engagement surface about a perimeter of the chamber of the barrel. The method further includes the step of partially withdrawing the plunger assembly from a position proximate to the distal end of the syringe barrel in a proximal direction so as to aspirate the chamber of the syringe barrel. The method also includes the steps of advancing the plunger assembly within the chamber of the syringe barrel, and retaining the plunger head in a locked position at least partially within the chamber of the barrel by perimetrical engagement with the retaining ring lock.

Further details and advantages of the invention will become clear upon reading the following detailed description in conjunction with the accompanying drawing figures, wherein like parts are designated with like reference numerals throughout.

DESCRIPTION OF PREFERRED EMBODIMENTS

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and embodiments. It is also to be understood that the specific devices illustrated in the accompanying drawing figures and described herein are simply exemplary and should not be considered as limiting.

Figure 1:
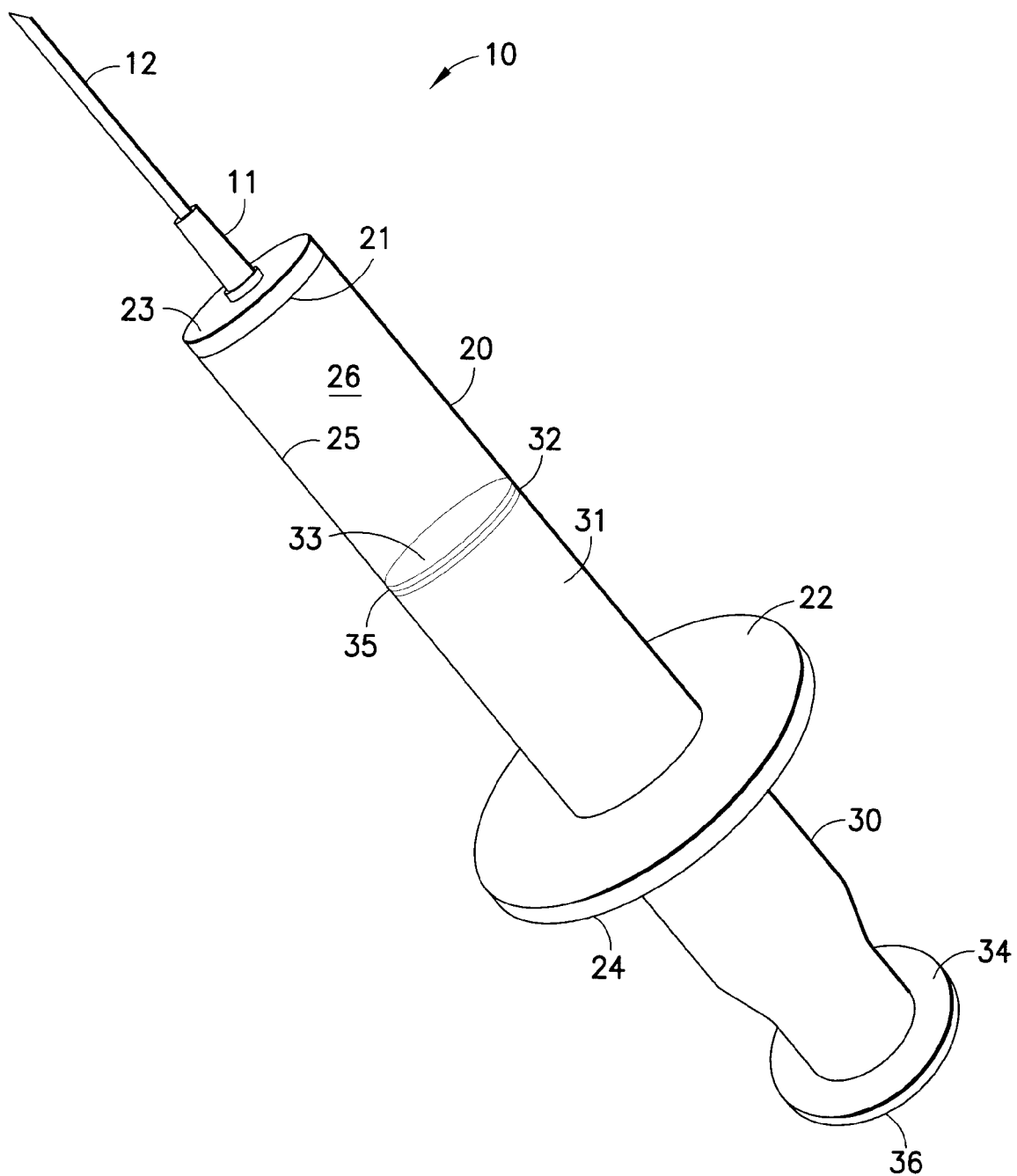
FIG. 1 is a perspective view of a perceived passive reuse prevention syringe in accordance with an embodiment of the present invention.

Referring to FIG. 1, a syringe assembly 10 is shown according to an embodiment of the present invention. The syringe assembly 10 includes a syringe barrel 20 and a plunger assembly 30. As shown in FIG. 1, the syringe barrel 20 has an inside surface 25, which defines a chamber 26. The syringe barrel 20 also includes an open proximal end 24 and an outlet 11 disposed on a distal end 23 of the syringe barrel 20. The outlet 11 is in fluid communication with the chamber 26 of the syringe barrel 20. A needle cannula 12 is attached to the syringe barrel 20 adjacent the outlet 11 such that an interior of the needle cannula 12 is in fluid communication with the chamber 26 of the syringe barrel 20. As shown, the syringe barrel 20 may have a cylindrical or substantially cylindrical shape, and may include an outwardly extending flange 22 at the open proximal end 24, though it is to be appreciated that the syringe barrel 20 may be formed in any suitable shape. Additionally, the syringe barrel 20 may be injection molded from thermoplastic material such as polypropylene and polyethylene according to techniques known to those of ordinary skill in the art, though it is to be appreciated that the syringe barrel may be made from other suitable materials, including glass, and according to other applicable techniques. Further, a retaining ring lock 21, which acts as a locking mechanism disposed within the chamber 26 of syringe barrel 20, is integrally molded or attached to the inside surface 25 of the syringe barrel 20. The retaining ring lock 21, as shown, is disposed within the chamber 26 of the syringe barrel 20 at a position proximate to the distal end 23 of the syringe barrel 20, though it is to be appreciated that the retaining ring lock 21 may be disposed at any position on the inside surface 25 of the syringe barrel 20 so long as the retaining ring lock 21 is positioned to effectively prevent reuse of the syringe assembly 10.

As shown in FIG. 1, the plunger assembly 30 has a distal end 35 and a proximal end 36 and extends within the syringe barrel 20. The plunger assembly 30 includes an elongate plunger rod 31 and a plunger head 32 having a distal sealing surface 33 disposed at the distal end 35 of the plunger assembly 30. The plunger rod 31 and the plunger head 32 may each have a substantially cylindrical shape and the plunger rod 31 may include an outwardly extending flange 34 at the proximal end of the plunger rod 31, which is also the proximal end 36 of the plunger assembly 30. It is to be appreciated that the plunger rod 31 and the plunger head 32 may be formed in any suitable shape so long as both the plunger rod 31 and the plunger head 32 conform to the shape of the inside surface 25 of the syringe barrel 20 such that the plunger assembly 30 effectively seals the chamber 26 of the syringe barrel 20 from the open proximal end 24 of the syringe barrel 20. To that end, the plunger rod 31 and the plunger head 32 may each have a width substantially equal to a width of the chamber 26 of the syringe barrel 20. Additionally, the plunger assembly 30 may be injection molded from thermoplastic material such as polypropylene, polyethylene, and polystyrene according to techniques known to those of ordinary skill in the art, though it is to be appreciated that the syringe barrel may be made from other suitable materials and according to other applicable techniques.

Figure 2:
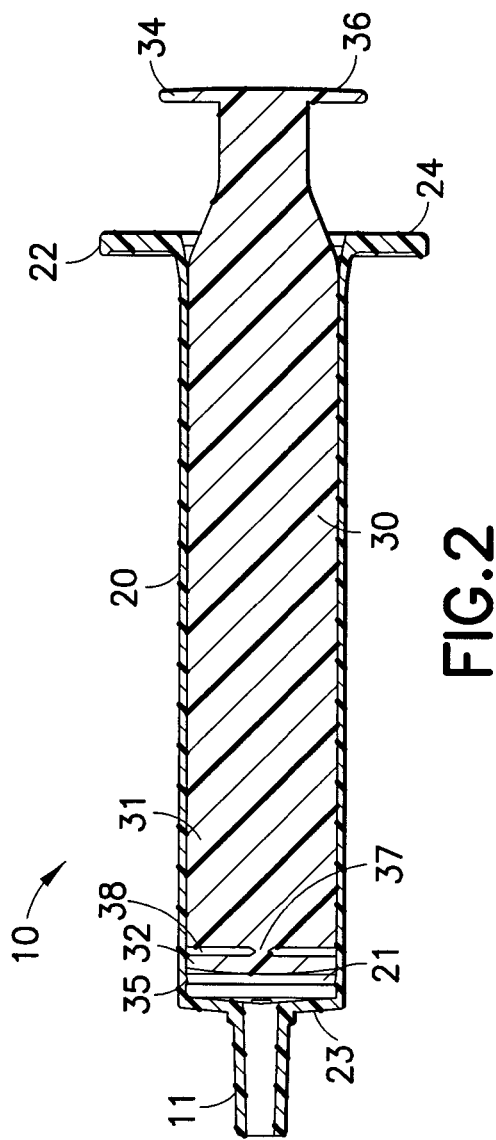
FIG. 2 is a cross-sectional side view of the perceived passive reuse prevention syringe of FIG. 1 in an initial state prior to use.
Figure 3:
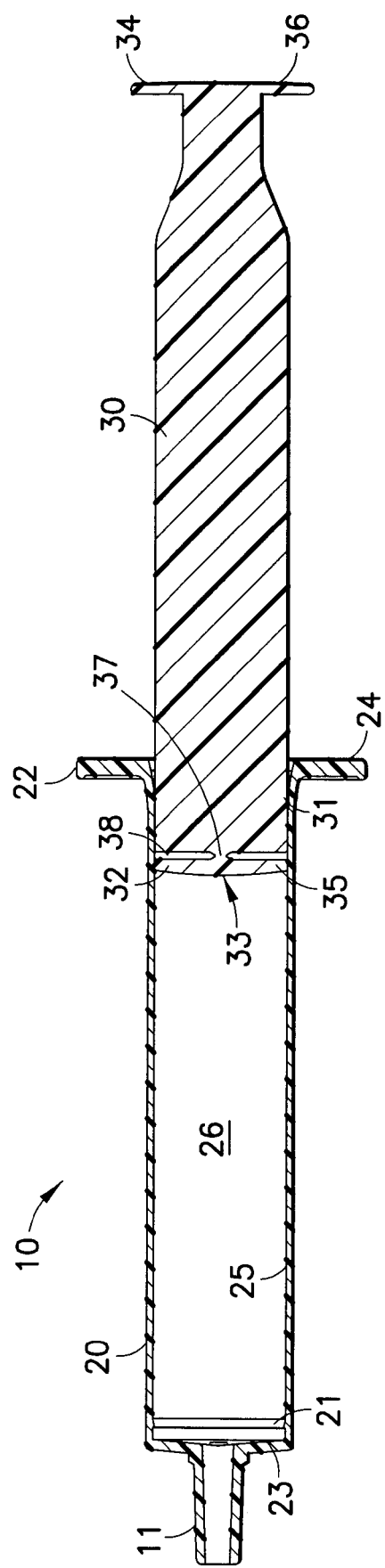
FIG. 3 is a cross-sectional side view of the perceived passive reuse prevention syringe of FIG. 1 after aspiration of the syringe.

As shown in FIGS. 2 and 3, the plunger assembly 30 is formed as a single, continuous piece with the plunger rod 31 and the plunger head 32 being integrally connected by a breakable neck portion 37 extending between a distal end surface 322 (shown in FIG. 5) of the plunger rod 31 and a proximal end surface 321 (shown in FIG. 5) of the plunger head 32. The breakable neck portion 37 has a substantially smaller width than the width of the plunger head 32 and the width of the plunger rod 31 such that an annular recess 38 is formed within the plunger assembly 30 between the plunger head 32 and the plunger rod 31.

Figure 4:
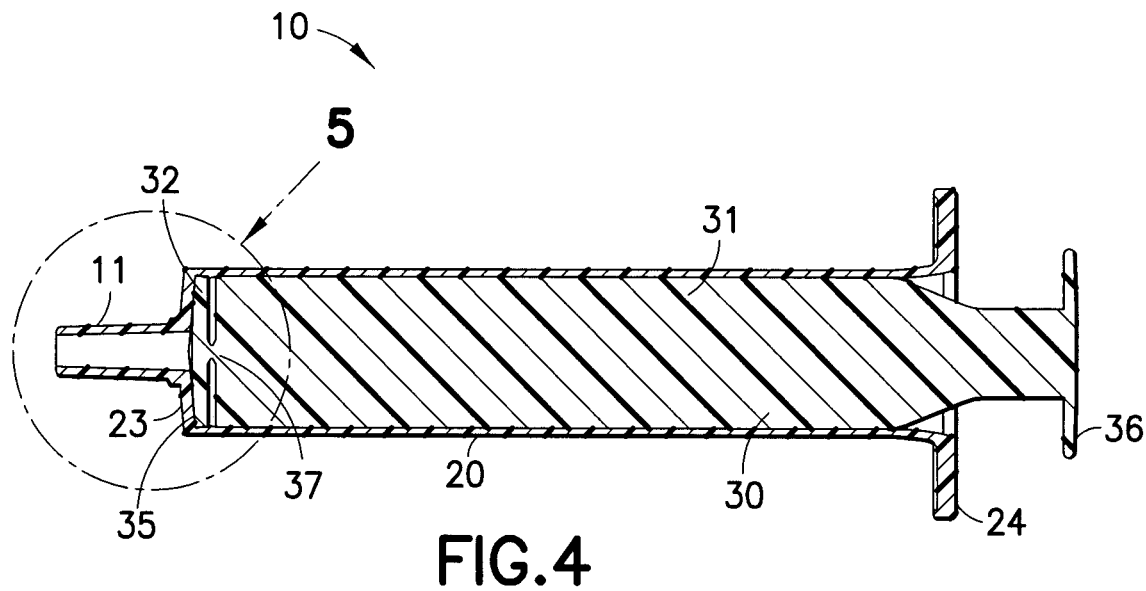
FIG. 4 is a cross-sectional side view of the perceived passive reuse prevention syringe of FIG. 1 after injection of the contents of the syringe, and with a plunger being situated in a locked position.
Figure 5:
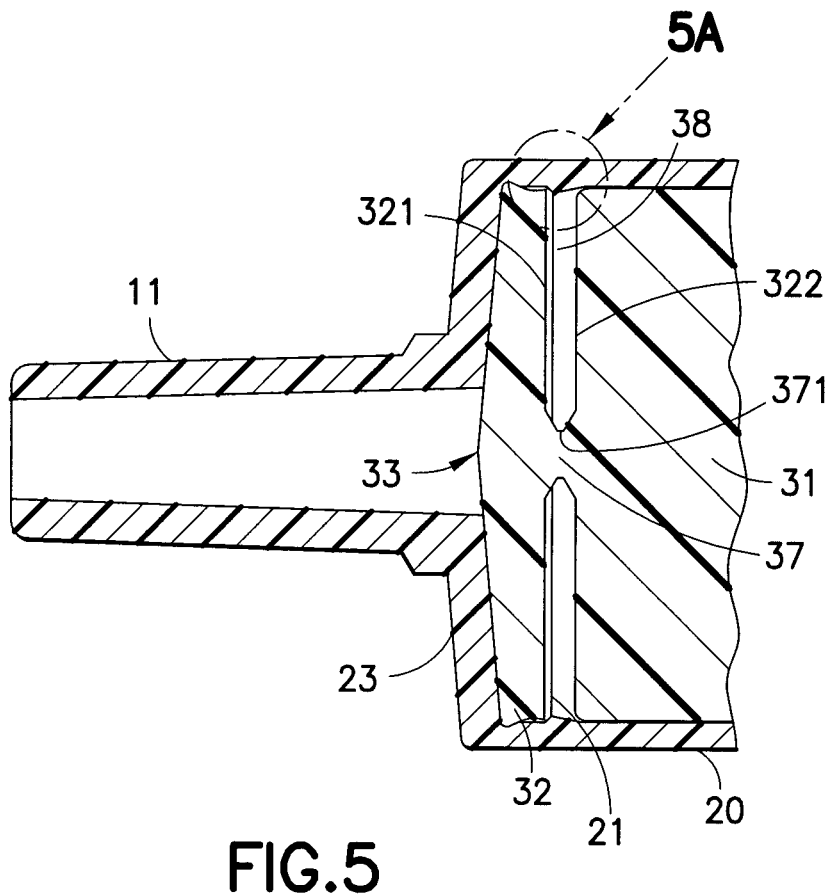
FIG. 5 is an enlarged sectional view of FIG. 4.
Figure 5A:
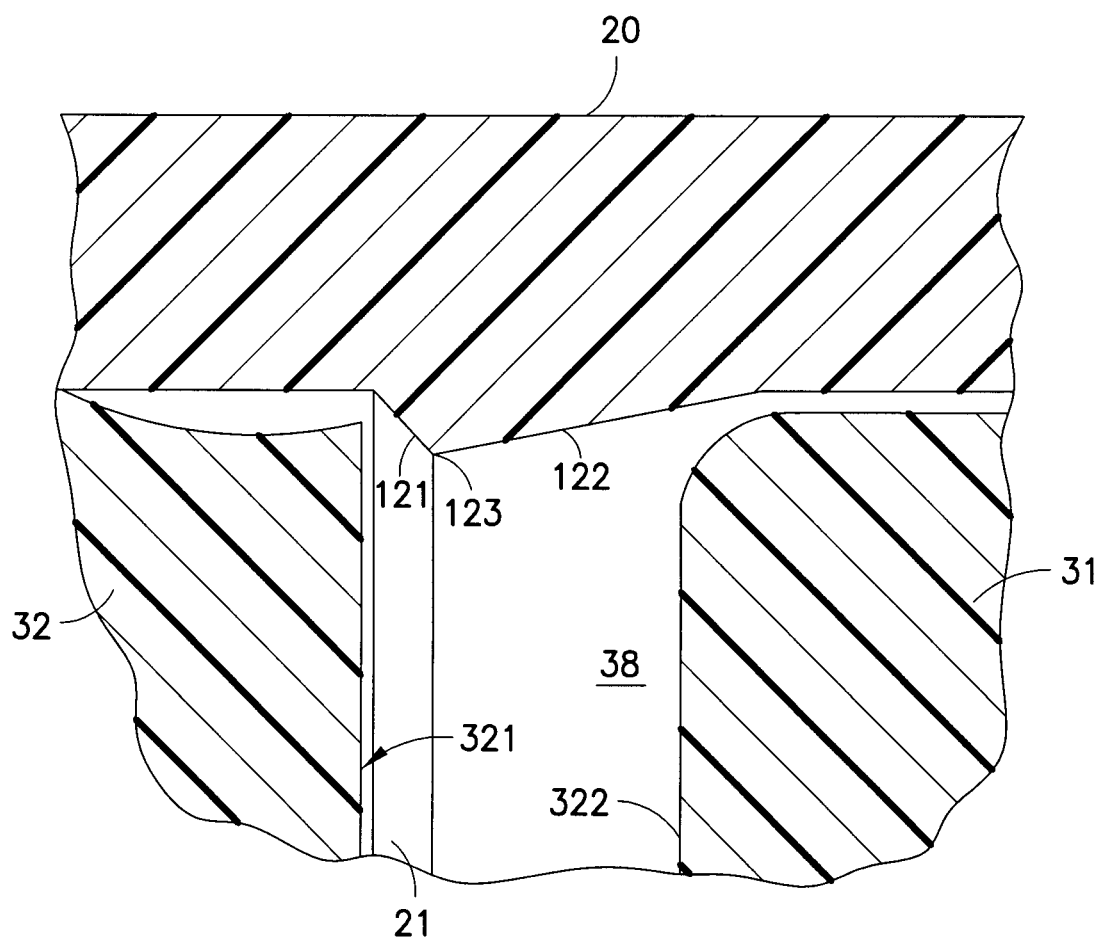
FIG. 5A is an enlarged sectional view of FIG. 5.

Referring to FIGS. 4, 5, and 5A, the retaining ring lock 21 is disposed on the inside surface 25 of the syringe barrel 20 adjacent the distal end 23 of the syringe barrel 20 so as to retain the plunger head 32 in a locked position within the chamber 26 of the syringe barrel 20 adjacent to the outlet 11 at the distal end 23 of the syringe barrel 20 following full injection of the contents of the syringe assembly 10. As shown in FIGS. 4 and 5, the retaining ring lock 21 engages the plunger head 32 so as to retain the plunger head 32 in the locked position while allowing the plunger rod 31 to be removed from the chamber 26 of the syringe barrel 20. As shown in FIG. 5, the plunger head 32 has an increased width, which is greater than a width of the plunger head 32 at the proximal end surface 321 slightly greater than a width of the chamber 26 of the syringe barrel 20, at the distal sealing surface 33 so as to engage the inside surface 25 of the syringe barrel 20 in order to seal the chamber 26. Also, the sealing surface 33 is shaped to conform to the shape of the distal end 23 of the syringe barrel 20 in order to seal the outlet 11 from fluid communication with the chamber 26 when the plunger head 32 is in the locked position. Thus, the plunger head 32 is sized and shaped to effectively seal the chamber 26 of the syringe barrel 20 without requiring a rubber stopper or plug to be disposed on the distal end of the plunger assembly 20. Alternatively, the plunger head 32 may be provided with a rubber coating or cover in order to facilitate a sealing engagement between the plunger head 32 and the inside surface 25 of the syringe barrel 20.

As shown in FIG. 5A, the retaining ring lock 21 has a substantially V-shaped cross-section extending into the chamber 26 of the syringe barrel 20 from the inside surface 25 of the syringe barrel 20 to an apex point 123. The retaining ring lock 21 has a proximal beveled surface 122 that is relatively long with a low taper so that the surface 122 engages the distal sealing surface 33 of the plunger head 32 such that the plunger head 32 is slidable past the retaining ring lock 21 in a distal direction. A distal beveled surface 121 of the retaining ring lock 21 is relatively short with a high taper so that the surface 121 engages the proximal end surface 321 of the plunger head 32 such that the plunger head 32 is restrained from sliding past the retaining ring lock 21 in a proximal direction.

Figure 5B:
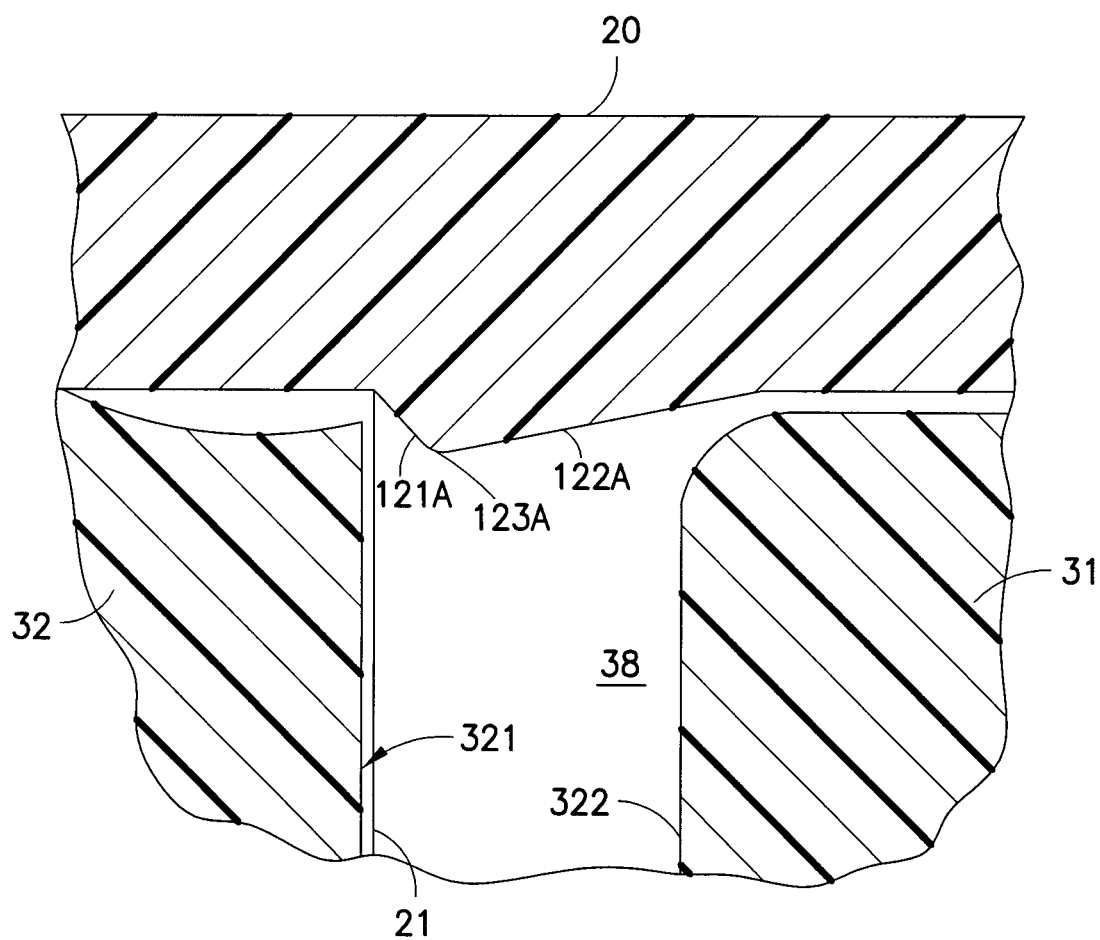
FIG. 5B is an enlarged sectional view of FIG. 5 illustrating a further embodiment of the present invention.

As shown in FIG. 5B, the retaining ring lock 21 may alternatively have a substantially V-shaped cross-section extending to a rounded apex 123A. The retaining ring lock 21 has a proximal surface 122A that is relatively long with a low taper so that the surface 122A engages the distal sealing surface 33 of the plunger head 32 such that the plunger head 32 is slidable past the retaining ring lock 21 in a distal direction. A distal surface 121A of the retaining ring lock 21 is relatively short with a high taper so that the surface 121A engages the proximal end surface 321 of the plunger head 32 such that the plunger head 32 is restrained from sliding past the retaining ring lock 21 in a proximal direction.

Figure 5C:
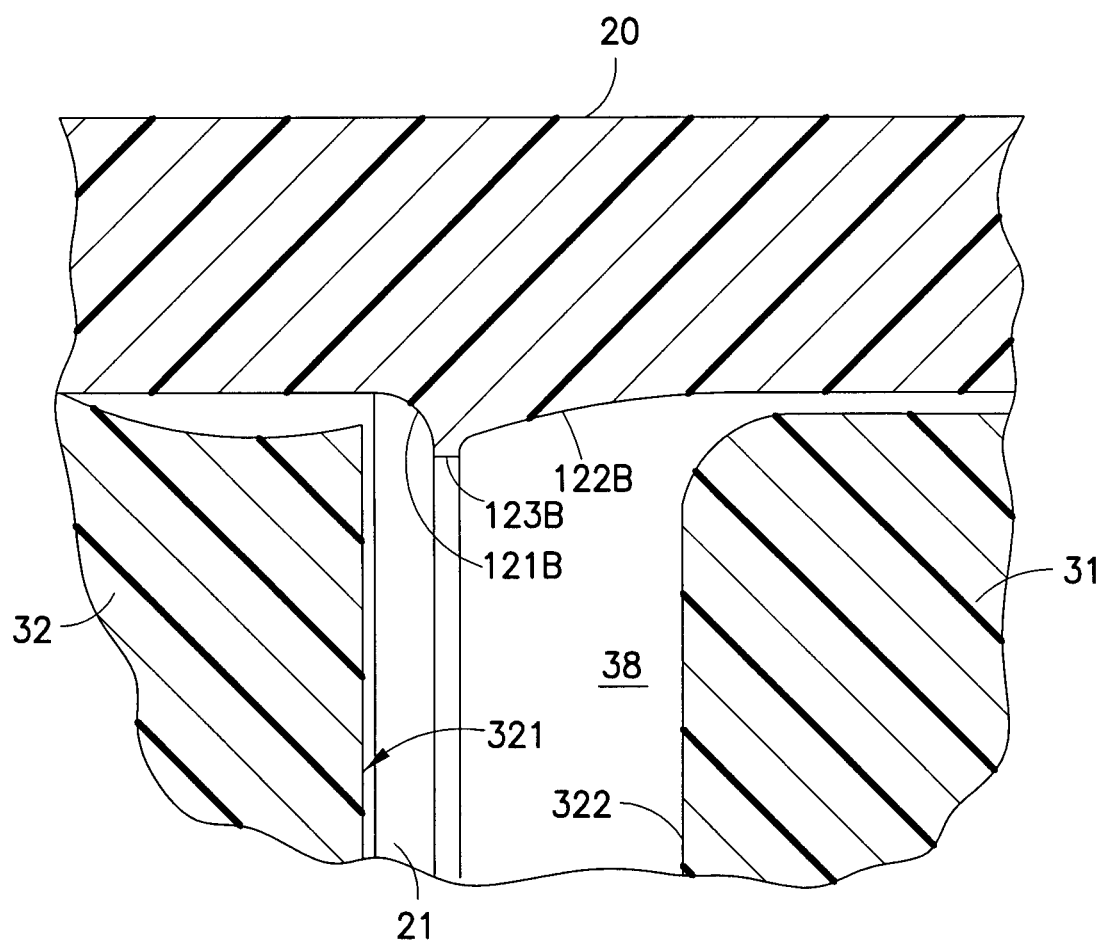
FIG. 5C is an enlarged sectional view of FIG. 5 illustrating a further embodiment of the present invention.

As shown in FIG. 5C, the retaining ring lock 21 may also alternatively have a substantially V-shaped cross-section extending to a flat apex 123B. The retaining ring lock 21 has a curved proximal surface 122B that is relatively long with a low amount of curvature so that the surface 122B engages the distal sealing surface 33 of the plunger head 32 such that the plunger head 32 is slidable past the retaining ring lock 21 in a distal direction. A curved distal surface 121B of the retaining ring lock 21 is relatively short with a high amount of curvature so that the surface 121B engages the proximal end surface 321 of the plunger head 32 such that the plunger head 32 is restrained from sliding past the retaining ring lock 21 in a proximal direction.

As shown in FIGS. 1, 5, and 5A, the proximal end surface 321 of the plunger head 32 has a continuous, non-flanged, non-segmented perimeter. Likewise, the retaining ring lock 21 extends entirely around the inside surface 25 of the syringe barrel 20 so as to surround the chamber 26 of the syringe barrel 20. As such, the distal beveled surface 121 of the retaining ring lock 21 defines a continuous non-segmented engagement surface about a perimeter of the chamber 26 of the syringe barrel 20. Thus, when the plunger head 32 is disposed within the locked position, the continuous engagement surface (distal beveled surface 121) of the retaining ring lock 21 engages the continuous perimeter of the proximal end surface 321 of the plunger head 32 in a continuous perimetrical engagement defined by a complete engagement between the continuous perimeter, the proximal end surface 321 of the plunger head 32, and the distal beveled surface 121.

The continuous perimetrical engagement between the proximal end surface 321 and the distal beveled surface 121 of the retaining ring lock 21 serves to prevent canting of the plunger head 32 with respect to the syringe barrel 20 as a user attempts to withdraw the plunger assembly 30 from the syringe barrel 20 after the plunger head 32 has entered the locked position and the plunger rod 31 is separated from the plunger head 32, as will be described below. Specifically, as a user pulls on the plunger rod 31, there will be a tendency to wiggle or pull on the plunger rod 31 at an angle in order to break the plunger rod 31 away from the plunger head 32 or to withdraw the plunger head 32 from the locked position. Such wiggling or pulling could cause the plunger head 32 to become canted or angled with respect to the syringe barrel 20, which may result in disruption of the sealing engagement between the distal sealing surface 33 of the plunger head 32 and the inside surface 25 of the syringe barrel or the improper delivery of extra dosage to a patient caused by rocking of the plunger head 32 within the chamber 26 of the syringe barrel 20 forcing out small quantities of the contents of the syringe barrel 20 remaining within the outlet 11 or the needle cannula 12 after full injection.

Figure 7:
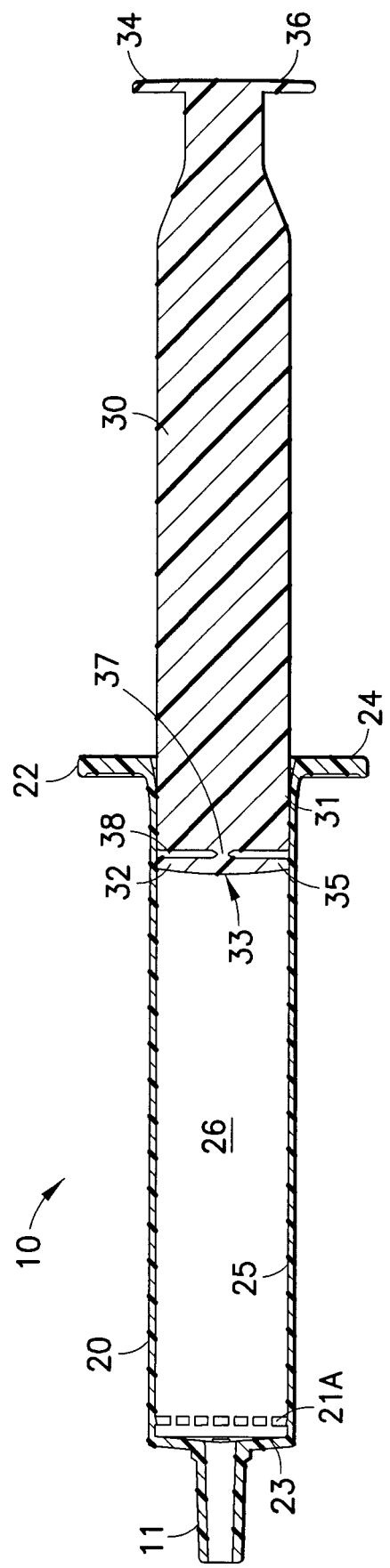
FIG. 7 is a cross-sectional side view of the perceived passive reuse prevention syringe of FIG. 1 according to a further embodiment of the present invention.

With reference to FIG. 7, the retaining ring lock 21A, according to a further embodiment, may be discontinuous. As shown, the retaining ring lock 21A is made up of a plurality of separate discontinuous segments disposed completely around the inside surface 25 of the syringe barrel 20 so as to surround the chamber 26 of the syringe barrel 20. When the plunger head 32 is disposed within the locked position, the engagement surface of each segment of the retaining ring lock 21A engages the continuous perimeter of the proximal end surface 321 of the plunger head 32 in a perimetrical engagement defined by an engagement between the continuous perimeter, the proximal end surface 321 of the plunger head 32, and the engagement surfaces of the segments of the retaining ring lock 21A.

Figure 6:
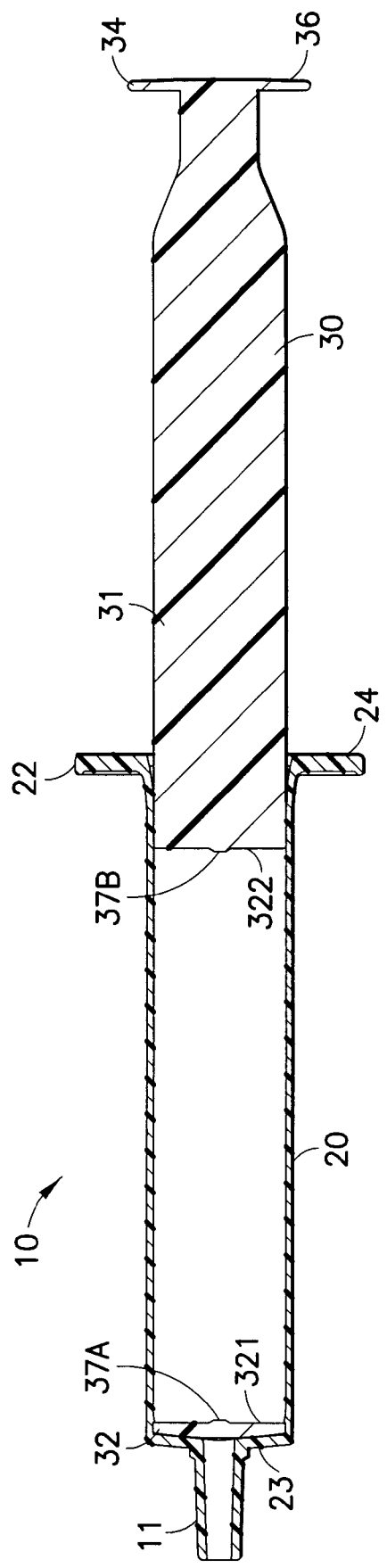
FIG. 6 is a cross-sectional side view of the perceived passive reuse prevention syringe of FIG. 1 with the locked plunger being broken into two pieces.

Referring to FIGS. 4, 5, and 6, the breakable neck portion 37 has a center 371 disposed between the proximal end surface 321 of the plunger head 32 and the distal end surface 322 of the plunger rod 31. The breakable neck portion 37 includes inwardly tapered portions extending from both surfaces 321, 322 so as to have a reduced diameter at the center 371. As such, the axial strength of the breakable neck portion 37 is reduced at the center 371 and the breakable neck portion 37 is adapted to break upon application of a sufficient axial force to the plunger rod 31 in the proximal direction.

As shown in FIG. 6, once full injection of the contents of the chamber 26 of the syringe barrel 20 is completed and the plunger head 32 is retained in the locked position distal of the retaining ring lock 21, pulling on the plunger rod 31 in a distal direction will result in the breakable neck portion 37 breaking apart at or near the center 371 such that the plunger head 32 remains in the locked position at least partially within the chamber 26 of the syringe barrel 20 due to the continuous perimetrical engagement between the proximal end surface 321 of the plunger head 32 with the distal beveled surface 121 of the retaining ring lock 21 while the plunger rod 31 is separated from the plunger head 32 and may be removed from the chamber 26 of the syringe barrel 20. Nub portions 37A, 37B remain on the proximal end surface 321 of the plunger head 32 and the distal end surface 322 of the plunger rod 31, respectively, after the breakable neck portion 37 has been broken.

Thus, reuse of the syringe assembly 10 after full injection and disposal of the plunger head 32 in a locking position distal of the retaining ring is prevented as the plunger assembly 30 will be broken into two pieces if a person attempts to withdraw the plunger assembly 30 from the syringe barrel 20 or re-aspirate the chamber 26 of the syringe barrel 20. It is to be appreciated that the breakable neck portion 37 may be structured to break upon application of any force to the plunger rod 31 by a user, though the breaking force 37 required to break the breakable neck portion and separate the plunger rod 31 from the plunger head 32 should be greater than a force necessary to at least partially aspirate the chamber 26 of the syringe barrel 20 but less than a force necessary to withdraw the plunger head 32 past the retaining ring lock 21. Particularly, the breaking force may only be slightly greater than the greatest force necessary to aspirate the chamber 26 of the syringe barrel 20.

Referring to FIGS. 2-6, operation of the syringe 10 according to an embodiment of the present invention will now be described in detail. As shown in FIG. 2, at an initial or packaged state, the plunger rod 31 is disposed at least partially within the chamber 26 of the syringe barrel 20 such that the plunger head 32 is situated proximate to the distal end 23 of the syringe barrel 20 and adjacent to the retaining ring lock 21. The plunger assembly 30 is then partially withdrawn in the proximal direction so as to aspirate the chamber 26 of the syringe barrel 20 and fill the syringe 10, as is shown in FIG. 3. Pushing the plunger assembly 30 distally when in the packaged state could result in premature locking of the syringe. So long as the plunger head 32 remains unlocked, the syringe 10 can be used as normal for aspiration and filling of the chamber 26 of the syringe barrel with a medicine or vaccine from a vial or other fluid source and then injection of a patient with the medicine or vaccine via the needle cannula 12. Alternatively, the syringe 10 can be used as normal for the re-constitution of dry drugs. Because the plunger assembly 30 remains unlocked prior to full injection of the contents of the chamber 26 of the syringe barrel 20, the syringe 10 allows for variable dosing since the chamber 26 of the syringe barrel 20 can be aspirated to hold varying volumes and its contents can be partially injected without locking the plunger head 32. Alternatively, the syringe 10 can be adapted to provide only fixed doses.

Once the desired aspiration of the chamber 26 of the syringe barrel 20 is completed, the plunger assembly 30 is advanced within the chamber 26 of the syringe barrel 20. As shown in FIGS. 4-6, once the plunger head 32 passes the retaining ring 21 upon full injection of the contents of the chamber 26 of the syringe barrel 20, the plunger head 32 passes the retaining ring lock 21 and is retained in a locked position at least partially within the chamber 26 of the syringe barrel 20 by the continuous perimetrical engagement with the retaining ring lock 21 and thus cannot be pulled back in the proximal direction. If a person attempts to withdraw the plunger head 32 from the locked position by pulling on the plunger head 32, the plunger rod 31 will break away from the plunger head 32 at the breakable neck portion 37 as described above. The plunger rod 31 may then be removed from the chamber 26 of the barrel 20. The plunger head 32 will remain in the locked position, blocking the chamber 26 of the syringe barrel 20 and sealing the outlet 11, thus rendering the syringe 10 completely disabled.

It is to be appreciated that the locking and reuse prevention mechanism of the present invention is a perceived passive mechanism in that it allows the syringe 10 to be used as a normal, traditional syringe without automatically locking or preventing reuse but will become locked and disabled by the user through normal operation of the syringe 10 and full injection of the contents of the syringe 10. Typically, the plunger head 32 will become locked in the syringe barrel 20 and the syringe 10 disabled without the user realizing that the locking mechanism has been actuated. Thus, a user of the syringe 10 perceives that the user has passively locked and disabled the syringe and that the locking mechanism automatically disables the syringe 10 after the syringe 10 has bottomed out upon full injection of the contents of the syringe 10.

While several embodiments of a perceived passive reuse prevention syringe that uses a retaining ring lock and method were described in the foregoing detailed description, those skilled in the art may make modifications and alterations to these embodiments without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are embraced within their scope.

What is claimed is:

1. A syringe assembly, comprising:
   a syringe barrel having an inside surface defining a chamber, an open proximal end, a distal end, and an outlet disposed adjacent the distal end in fluid communication with the chamber;
   a plunger assembly disposed at least partially within the syringe barrel, comprising an elongate plunger rod and a plunger head having a distal sealing surface and a proximal end surface, the proximal end surface of the plunger head having a continuous perimeter and the plunger rod and the plunger head being integrally connected; and
   a retaining ring lock disposed on the inside surface of the barrel and extending into the chamber of the barrel and defining an engagement surface about a perimeter of the chamber of the barrel, the retaining ring lock adapted to engage and retain the plunger head in a locked position at least partially within the chamber of the barrel,
   wherein the engagement surface of the retaining ring lock engages the continuous perimeter of the proximal end surface of the plunger head in a perimetrical engagement when the plunger head is in the locked position, and
   wherein the plunger assembly is formed as a single, monolithic piece.

2. The syringe assembly according to claim 1, wherein the plunger head has a width slightly greater than a width of the chamber of the barrel at the distal sealing surface.

3. The syringe assembly according to claim 1, wherein the engagement surface of the retaining ring lock is continuous about the perimeter of the chamber of the barrel and the retaining ring lock engages the continuous perimeter of the proximal end surface of the plunger head in a continuous perimetrical engagement when the plunger head is in the locked position.

4. The syringe assembly according to claim 1, wherein the retaining ring lock is disposed within the chamber of the barrel adjacent the distal end of the barrel.

5. The syringe assembly according to claim 4, wherein the retaining ring lock retains the plunger head in the locked position within the chamber of the barrel adjacent the distal end of the barrel.

6. The syringe assembly according to claim 1, further comprising a needle cannula in fluid communication with the chamber of the barrel.

7. The syringe assembly according to claim 1, wherein the plunger assembly further includes a breakable neck portion extending between the plunger rod and the proximal end surface of the plunger head, the plunger rod and the plunger head being integrally connected by the breakable neck portion.

8. The syringe assembly according to claim 7, wherein the breakable neck portion comprises a tapered portion.

9. The syringe assembly according to claim 8, wherein the breakable neck portion has a center disposed between the proximal end surface of the plunger head and the distal end surface of the plunger rod, and tapers from both the proximal end surface of the plunger head and the distal end surface of the plunger rod so as to have a reduced diameter at the center.

10. The syringe assembly according to claim 7, wherein the breakable neck portion is adapted to break upon application of a force to the plunger rod that is greater than a force necessary to at least partially aspirate the syringe, and less than a force necessary to withdraw the plunger head past the retaining ring lock.

11. The syringe assembly according to claim 1, wherein the retaining ring lock is integral with the inside surface of the barrel.

12. The syringe assembly according to claim 11, wherein the retaining ring lock has a substantially V-shaped cross-section, a proximal beveled surface of the retaining ring lock engages the distal sealing surface of the plunger head such that the plunger head is slidable past the retaining ring lock in a distal direction, and the engagement surface of the retaining ring lock is a distal beveled surface of the retaining ring lock that engages the proximal end surface of the plunger head such that the plunger head is restrained from sliding past the retaining ring lock in a proximal direction.

13. The syringe assembly according to claim 11, wherein the retaining ring lock has a substantially V-shaped cross-section with a rounded apex, a proximal surface of the retaining ring lock that engages the distal sealing surface of the plunger head such that the plunger head is slidable past the retaining ring lock in a distal direction, and the engagement surface of the retaining ring lock is a distal surface of the retaining ring lock that engages the proximal end surface of the plunger head such that the plunger head is restrained from sliding past the retaining ring lock in a proximal direction.

14. The syringe assembly according to claim 11, wherein the retaining ring lock has a substantially V-shaped cross-section with a flat apex, a curved proximal surface of the retaining ring lock that engages the distal sealing surface of the plunger head such that the plunger head is slidable past the retaining ring lock in a distal direction, and the engagement surface of the retaining ring lock is a curved distal surface of the retaining ring lock that engages the proximal end surface of the plunger head such that the plunger head is restrained from sliding past the retaining ring lock in a proximal direction.

15. A plunger assembly for a syringe, the plunger assembly comprising:
    an elongate plunger rod;
    a plunger head having a distal sealing surface and a proximal end surface, the proximal end surface of the plunger head having a continuous perimeter adapted to provide a perimetrical engagement with a chamber of a syringe barrel; and
    a breakable neck portion extending between the plunger rod and the proximal end surface of the plunger head,
    wherein the plunger rod and the plunger head are integrally connected by the breakable neck portion,
    wherein the plunger assembly is formed as a single, monolithic piece, and
    wherein the breakable neck portion comprises a center disposed between the proximal end surface of the plunger head and the distal end surface of the plunger rod and tapered portions extend from both the proximal end surface of the plunger head and the plunger rod so as to have a reduced diameter at the center.

16. The plunger assembly according to claim 15, wherein the plunger head is adapted to engage a retaining ring lock disposed within a barrel of the syringe such that the plunger head is capable of being retained in a locked position at least partially within the barrel of the syringe.

17. The plunger assembly according to claim 16, wherein the breakable neck portion is adapted to break upon application of a force to the plunger rod that is greater than a force necessary to at least partially aspirate the syringe, and less than a force necessary to withdraw the plunger head past the retaining ring lock.

18. The plunger assembly according to claim 15, wherein the plunger head has a width at the distal sealing surface greater than a width of the plunger head at the proximal end surface.

* * * * *